(12) United States Patent
Einarsson et al.

(10) Patent No.: US 9,265,644 B2
(45) Date of Patent: Feb. 23, 2016

(54) WEARABLE DEVICE

(75) Inventors: Palmi Einarsson, San Juan Capistrano, CA (US); Arni Thor Ingimundarson, Ladera Ranch, CA (US)

(73) Assignee: OSSUR HF, Reykjavik (IS)

( * ) Notice: Subject to any disclaimer, the term of this patent is extended or adjusted under 35 U.S.C. 154(b) by 257 days.

(21) Appl. No.: 13/273,752

(22) Filed: Oct. 14, 2011

(65) Prior Publication Data

US 2012/0035518 A1 Feb. 9, 2012

Related U.S. Application Data

(63) Continuation of application No. 12/232,199, filed on Sep. 12, 2008, now Pat. No. 8,043,244.

(60) Provisional application No. 60/960,048, filed on Sep. 13, 2007.

(51) Int. Cl.
*A61F 5/01* (2006.01)
*B29C 45/00* (2006.01)
*B29C 45/16* (2006.01)
*B29L 31/00* (2006.01)

(52) U.S. Cl.
CPC ....... *A61F 5/0123* (2013.01); *A61F 2005/0148* (2013.01); *B29C 45/0081* (2013.01); *B29C 45/1676* (2013.01); *B29L 2031/753* (2013.01)

(58) Field of Classification Search
CPC ... A61F 5/0123; A61F 5/0125; A61F 5/0109; A61F 2005/0139; A61F 5/0106; A61F 5/0111; A61F 5/0585; A61F 5/0102; A61F 5/0195; A61F 5/0127; A61F 5/3776; A61F 5/3715; A61F 5/055; A61F 5/3723; A01K 27/002; A01K 27/001; E05B 75/00

USPC ......... 602/5–8, 18–19, 20, 23–25, 26–27, 16, 602/62; 2/24, 463–465, 2.5; 24/265 R; 119/856; 128/876, 846; 224/257

See application file for complete search history.

(56) References Cited

U.S. PATENT DOCUMENTS

| | | | | |
|---|---|---|---|---|
| 3,817,244 | A | * | 6/1974 | Taylor .............................. 602/26 |
| 4,130,115 | A | * | 12/1978 | Taylor ................... A61F 5/0109 602/16 |
| 4,312,335 | A | | 1/1982 | Daniell, Jr. |
| 4,372,298 | A | | 2/1983 | Lerman |
| 4,381,768 | A | | 5/1983 | Erichsen et al. |
| 4,556,053 | A | | 12/1985 | Irons |

(Continued)

FOREIGN PATENT DOCUMENTS

WO WO9400082 1/1994

*Primary Examiner* — Ophelia A Hawthorne
(74) *Attorney, Agent, or Firm* — Workman Nydegger

(57) ABSTRACT

A wearable device includes a unitary first frame assembly which is integrally formed from first and second polymeric materials. The first frame assembly has a first frame portion formed by the first polymeric material and extends around part of a second frame portion formed by the second polymeric material. The first frame member includes a flexible first shell and a first connecting portion which depends from the first shell. The second frame portion forms part of the first shell and continuously extends to the first connecting portion without interruption. The second polymeric material has greater rigidity than the first polymeric material. The device also includes a second frame assembly having a second connecting portion which links to the first connecting portion.

2 Claims, 5 Drawing Sheets

(56) References Cited

U.S. PATENT DOCUMENTS

| | | | |
|---|---|---|---|
| D298,568 S | 11/1988 | Womack et al. | |
| 4,791,916 A | 12/1988 | Paez | |
| 4,966,133 A * | 10/1990 | Kausek | 602/16 |
| 5,306,230 A | 4/1994 | Bodine | |
| 5,624,389 A | 4/1997 | Zepf | |
| 5,814,002 A * | 9/1998 | Nelson | 602/27 |
| 5,823,931 A * | 10/1998 | Gilmour | 602/24 |
| 5,891,071 A | 4/1999 | Stearns | |
| 6,142,965 A | 11/2000 | Mathewson | |
| 6,287,268 B1 | 9/2001 | Gilmour | |
| 6,401,245 B1 * | 6/2002 | Slautterback | A41D 13/065 2/24 |
| 6,740,054 B2 | 5/2004 | Stearns | |
| 7,198,610 B2 | 4/2007 | Ingimundarson et al. | |
| 7,862,527 B2 * | 1/2011 | Gramza | A61F 5/0106 602/23 |
| 7,867,183 B2 * | 1/2011 | Kazmierczak | A61F 5/0123 602/23 |
| 7,870,982 B2 * | 1/2011 | Dong | A45F 3/14 224/257 |
| 2002/0107464 A1 | 8/2002 | Castillo | |
| 2004/0002674 A1 | 1/2004 | Sterling | |
| 2006/0135900 A1 | 6/2006 | Ingimundarson et al. | |
| 2007/0185425 A1 | 8/2007 | Einarsson et al. | |
| 2008/0195014 A1 | 8/2008 | Ingimundarson et al. | |
| 2009/0044808 A1 * | 2/2009 | Guney | A61M 16/0666 128/206.24 |

* cited by examiner

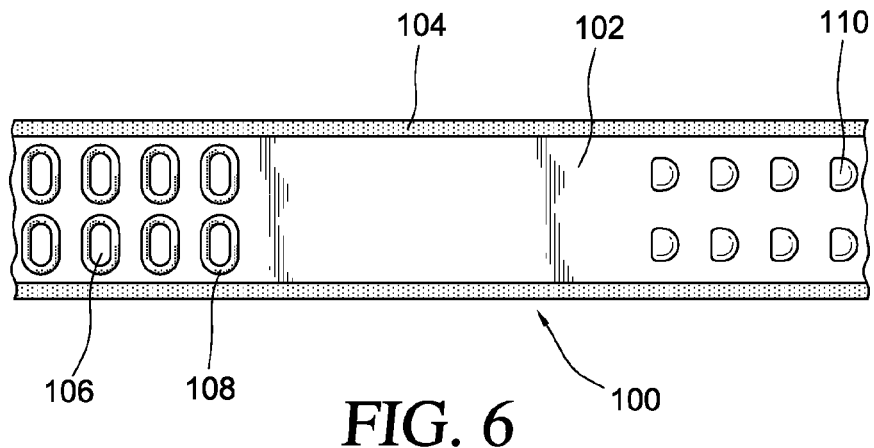
FIG. 6
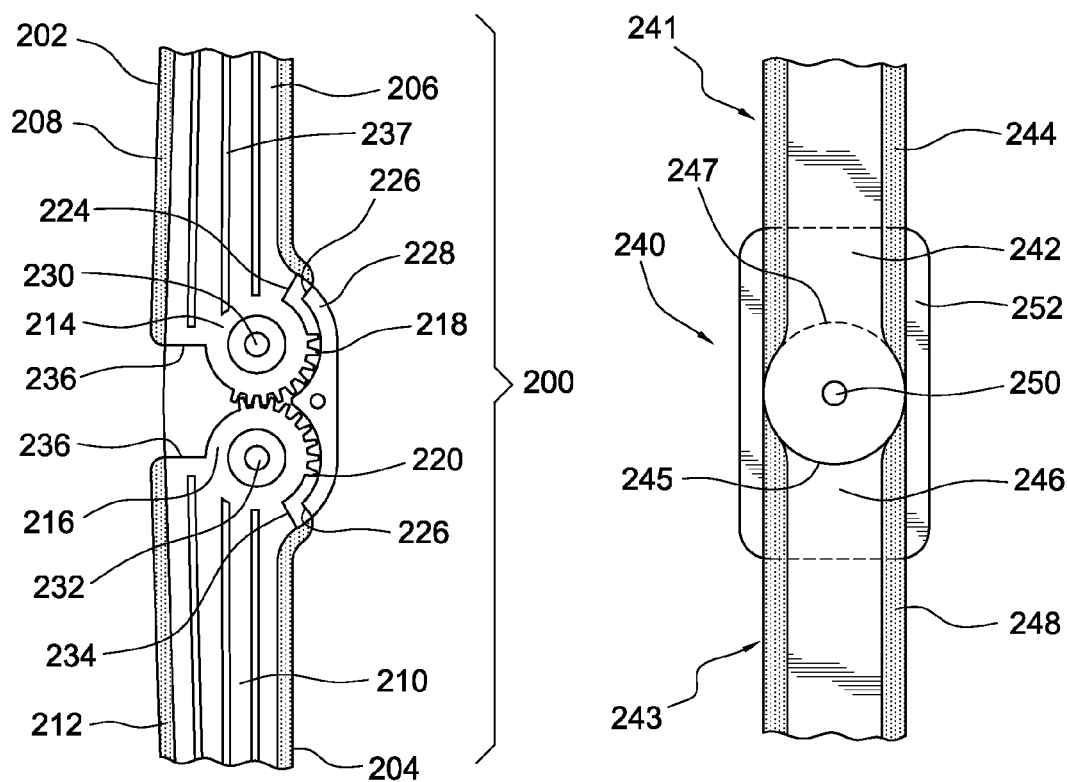
FIG. 7
FIG. 8

WEARABLE DEVICE

CROSS-REFERENCE TO RELATED APPLICATION

This application is a continuation of U.S. patent application Ser. No. 12/232,199, filed on Sep. 12, 2008, now U.S. Pat. No. 8,043,244, which claims the benefit of U.S. Provisional Application No. 60/960,048, filed Sep. 13, 2007.

FIELD OF THE INVENTION

The present invention relates generally to the field of wearable devices, such as those pertaining to orthopedic and prosthetic applications, and more particularly to a wearable device that provides stability, protection, support, rehabilitation, and/or unloading to a portion of the human anatomy in a streamlined and light manner.

BACKGROUND

A variety of wearable devices are available for orthopedic and prosthetic applications for providing stability, protection, support, rehabilitation and/or unloading a portion of the human anatomy. Known devices, however, are often associated as being bulky and heavy, and further costly requiring numerous manufacturing processes to produce.

An example of a wearable device is a knee brace. As is well understood, knee braces are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm, a knee brace may stabilize, protect, support, unload, and/or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs.

A healthy knee has an even distribution of pressure in both the medial and lateral compartments of the knee. It is normal for a person with a healthy knee to place a varus moment on the knee when standing so that the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or simply due to aging of the knee.

A major problem resulting from osteoarthritis of the knee is that the smooth cartilage lining the inside of the knee wears away. This leads to a narrowing of the joint space with the development of cysts and erosions in the bone ends. Because of the narrowing of the joint, bone comes directly in contact with bone, and an uneven distribution of pressure develops across the knee which may result in the formation of bone spurs around the joint. All of these changes ultimately lead to increasing pain and stiffness of the joint.

While there are no cures to osteoarthritis, there are many treatments. Individuals who have a diagnosis of isolated lateral or medial compartmental osteoarthritis of the knee are confronted with a variety of treatment options such as medications, surgery, and nonsurgical interventions. Nonsurgical interventions include the use of canes, lateral shoe wedges, and knee bracing.

Knee bracing is useful to provide compartment pain relief by reducing the load on the compartment through the application of an opposing external valgus or varus moment about the knee joint. Unloading knee braces have been shown to significantly reduce osteoarthritis knee pain while improving knee function.

While known knee braces are successful at reducing pain or at stabilizing a knee joint, many users find these braces to be bulky, difficult to don, complicated to configure, and uncomfortable to wear. For these reasons, the exemplary embodiments described herein have streamlined features capable of providing relief for medial or lateral compartmental osteoarthritis, or functional stability of the knee without the attendant drawbacks of known unloading knee braces.

The concepts described in connection with the exemplary knee brace embodiments may be extended to a variety of wearable devices that are configured to be secured to and/or support numerous portions of anatomy.

SUMMARY

The wearable device disclosed herein may be provided in the form of an unloading type knee brace, in accordance with the principles described in U.S. Pat. No. 7,198,610, granted Apr. 3, 2007, and incorporated herein by reference.

The exemplary wearable device disclosed herein provides a lightweight, low cost alternative to existing knee braces by providing a unitary knee brace that has a frame defined by a continuously formed proximal shell, hinge, and distal shell. Thus the entire frame and hinge assembly may be continuously formed in a one piece construction, for example, by the use of injection molding techniques. Overmolding techniques and materials, such as those described in U.S. patent application publication 2008/0195014, and incorporated herein by reference, may be utilized to form the unitary frame and hinge, such that the proximal and distal shell members are substantially flexible, while the hinge has a greater stiffness than the proximal and distal shell members.

Further, with the addition of at least one strap that may also be formed by injection molding techniques and which is vastly adjustable, a highly versatile, lightweight, and low cost unitary knee brace is provided that may be sold off-the-shelf or over-the-counter to many different persons having a variety of different leg geometries.

The knee brace may incorporate injection molding and overmolding techniques to create a unitary frame and hinge. The frame thus formed may define at least two discrete regions of materials with the first region having a greater stiffness than the second region, or vice versa. Preferably, the frame is continuously formed such that the thicknesses of the shells blend into portions of the hinge so as to secure these components together.

In a particular embodiment, the knee brace has a unitary frame defined by a proximal shell, a hinge continuously extending from the proximal shell, and a distal shell continuously extending from the hinge. The proximal and distal shells and hinge may define the first region of greater stiffness centrally located along the proximal and distal shells, and the hinge, and the second region generally surrounding and bordering the first region at the proximal and distal shells.

The proximal shell may define a proximal frame segment that extends from the proximal frame generally towards the distal frame. The proximal frame segment includes holes that provide ventilation, reduced weight, and flexibility. The proximal frame segment also includes a projection for connecting to a first strap connector.

A first strap assembly, which may also be formed by injection molding and/or overmolding techniques, is provided to connect to both the proximal and distal shells. The first strap assembly includes a first strap and a strap connector such that the first strap is selectively and adjustably positionable relative to the proximal shell via a first strap connector and is fixedly secured to the distal shell.

The first strap assembly may also include a buckle assembly having a locking device securable with an opening defined on the distal shell may be provided to removably secure the first strap to the distal shell. A flexible extension member may be provided to removably secure the first strap to the distal shell. In this manner, the first strap assembly may be adjusted to provide tightening and unloading forces to users having varied geometries of legs and knee joints, irrespective of the particular leg and knee geometry.

A second strap assembly having a similar configuration to the first strap assembly may also be provided for connection to the proximal and distal shells. The first and second strap assemblies may intersect or cross at a position generally opposed to the hinge. The first and second strap assemblies may include substantially inelastic portions, such as the strap connectors, so that they do not stretch when the knee brace is secured to the leg.

The hinge may have an undulating profile formed along the anterior and posterior faces thereof to aid with extension and flexion of the knee brace when the brace is secured to the leg. The hinge defines a geometry providing greater strength and stiffness than at least one of the proximal and distal shells such that the hinge permits translation of the proximal shell relative to the distal shell in flexion and extension directions.

The hinge may likewise be formed so as to limit a range of motion in the flexion and extension directions such that the hinge geometry is configured to resist rotation. For example, the hinge may be slightly biased in the flexion direction in that the hinge geometry has a predetermined bend favoring flexion, and limiting extension. However, the hinge geometry is preferably configured such that the hinge can only bend so far to a certain degree in the flexion direction.

The hinge may also define an undulating profile delimited by breaks formed along lateral and medial facing sides thereof to aid with varus/valgus rotation of the knee brace when the brace is secured to the leg. Or in the alternative, the hinge may be reinforced with elongate ribs running the length of the hinge to resist lateral and medial movement of the leg.

Additional features of the knee brace may include padding or ventilated padding material provided as an interface between the proximal and distal shells and a user's body, or between the straps and the user's body. Further, openings, holes, or slots may be provided in any or all of the shells and straps to aid with ventilation, reduce weight, and/or provide flexibility.

According to another embodiment of a wearable device, a unitary first frame assembly is integrally formed from at least first and second polymeric materials. A first frame portion is formed by the first polymeric material and extends around at least part of a second frame portion formed by the second polymeric material. The first frame member includes a flexible first shell and a first connecting portion depending from the first shell, and the second frame portion forms part of the first shell and continuously extends to the first connecting portion without interruption. The second polymeric material may have a greater rigidity than the first polymeric material.

The wearable device may also include a second frame assembly having a second shell and a second connecting portion linking to the first connecting portion.

In accordance with any of the embodiments described herein of a wearable device, a strap may be provided which is formed from at least two different polymeric materials each having different rigidity properties. The strap secures to the first shell and is selectively positionable at predetermined locations on the second shell. A first polymeric material may form a longitudinal core of the strap, and a second polymeric material may form a peripheral edge portion surrounding at least part of the longitudinal core. The first polymeric material has greater rigidity than the second polymeric material. This particular strap can be formed such that the longitudinal core is substantially inelastic whereas the peripheral edge portion is substantially soft thereby providing a pressure-relieving feature for the wearer of the device.

The numerous advantages, features and functions of embodiments of a wearable device will become readily apparent and better understood in view of the following description and accompanying drawings. The following description is not intended to limit the scope of wearable device, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIG. 6 is a plan view of an embodiment of a strap according to the wearable device;

FIG. 7 is an elevational view of an embodiment of a hinge device according to the wearable device; and FIG. 8 is an elevational view of another embodiment of a hinge device according to the wearable device.

Figure 2:
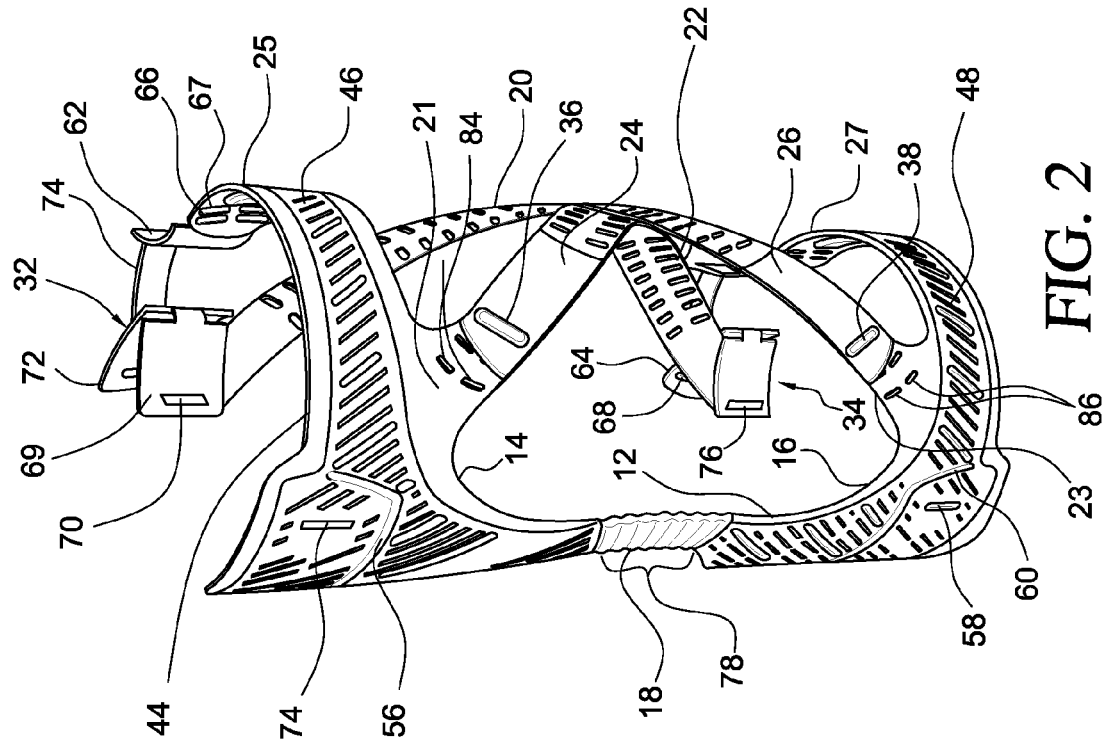
FIG. 2 is a front medial side perspective view of the knee brace of FIG. 1 with the straps of the brace unbuckled.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate an exemplary embodiment of a wearable device, and in no way limit the structures or configurations of a wearable device according to the present disclosure.

DETAILED DESCRIPTION OF VARIOUS EMBODIMENTS

A. Environment and Context

An embodiment of a wearable device in the form of a knee brace is provided to reduce the effect of osteoarthritis in a knee joint, or stabilize a knee joint that has been weakened by injury or other infirmities. Although the illustrated embodiment shows a hinge positioned on the medial side of the knee brace and the straps positioned on the lateral side of the knee brace, it will be understood that the knee brace may be configured to reduce or cure both medial and lateral knee joint infirmities, and thus, the hinge may be positioned on the lateral side of the knee brace and the straps may be positioned on the medial side of the knee brace.

The knee brace embodiment of the disclosure is particularly adapted for a human knee joint, and may be dimensioned to accommodate different types, shapes and sizes of human joints, appendages, and other anatomical portions. In addition, embodiments may be provided to orient principal forces exerted by strap systems of the embodiments at any desirable location to treat knee infirmities.

For explanatory purposes, the knee brace embodiment described herein is divided into sections which are denoted by general anatomical terms for the human body. Each of these terms is particularly used in reference to a human leg which is divided in similar sections with a proximal-distal plane generally extending along the meniscus of the knee between the femur and tibia (i.e., femoral and tibial leg portions, respectively).

The embodiment of the knee brace is also divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal plane and median, sagittal or lateral-medial planes.

The anatomical terms described herein are not intended to detract from the normal understanding of such terms as readily understood by one of ordinary skill in the art of orthotics. It will also be understood that, while the invention is discussed in connection with a knee brace, the principles described herein can be extended to a variety of orthopedic and prosthetic devices, and any other device that would be wearable and employ the features described herein.

B. Detailed Description of Wearable Device Embodiments

As discussed above, an exemplary embodiment of the wearable device is described by way of example by the embodiment of a knee brace. The knee brace disclosed herein may be of an unloading, osteoarthritic knee brace of a type generally described in U.S. Pat. No. 7,198,610, incorporated herein by reference. Accordingly, the description in connection with this particular embodiment focuses on the structure, materials, and configuration of a particular embodiment of an unloading, osteoarthritic knee brace, without belaboring the particular effects and modalities for treating osteoarthritis in the knee joint.

Referring to FIGS. 1-5, the knee brace 10 is suitable for stabilizing, protecting, supporting, unloading, and/or rehabilitating the knee. As shown, the knee brace 10 is composed of a unitary and continuously formed frame 12 that is configured to engage the limbs around, and support, the knee joint.

The unitary frame 12 includes a proximal (first) frame portion, assembly or shell 14, a hinge 18, and a distal (second) frame portion, assembly or shell 16. The proximal shell 14 has an extending portion along the medial side thereof that continuously forms the hinge 18. The hinge 18 extends along the medial side and is continuously formed with the distal shell 16. The proximal and distal shells have a flexible arcuate geometry capable of forming a variety of curvilinear profiles to accommodate a wearer's leg.

This continuous, unitary configuration of the proximal and distal shells 14, 16, and the hinge 18 may be formed in any suitable manner, such as by casting, machining, or injection molding. Materials for use as proximal and distal shells 14, 16, and the hinge 18 may include polymeric materials, carbon or glass fiber and epoxy composites, metals, such as aluminum, or any other suitable material. It will be recognized that different materials may be used for each of the components, while still maintaining the continuous, unitary construction of the knee brace 10.

As shown in FIGS. 1-4, the proximal and distal shells 14, 16 each include a main portion that extends along the medial side of the knee brace 10 and a substantially horizontally extending arcuate portion configured to extend around the anterior portion of the leg, and around the lateral side of the leg. The proximal and distal shells 14, 16 are suitably formed of a material that provides support to the knee joint and leg, while being flexible enough to allow the proximal and distal shells 14, 16 and the horizontally extending arcuate portions to conform to the geometry of the leg and knee joint of the user. It is understood that composite materials, polymeric materials, such as polyethylene, or metals, such as aluminum, are materials suitable to achieving support for the knee joint and leg while providing suitable flexibility.

The various components of the frame, including the proximal and distal shells, and the hinge, may be formed from different materials and connected together, or may be formed with areas having greater thicknesses than in other areas in order to strengthen certain areas of the frame relative to other areas.

In certain variations, these components of the frame may be formed without interruptions. For example, the proximal shell can be continuously formed with the hinge such that there is no structure (e.g., fasteners or glues) that connects the proximal shell to the hinge other than the materials forming these features, be it through mechanical or chemical interlocking. According to one variation, polymeric material forming part of the proximal shell continuously extends to form part of the hinge. This may be done while injection molding the proximal shell and at least a portion of the hinge together.

In another variation, a first polymeric material forming part of the proximal shell interlocks with apertures or other interlocking structure of the hinge. This may be done by first injection molding at least a part of the hinge and then injection molding the proximal shell over or partly over the already formed hinge. At least a portion of the hinge, however, can be formed from the first polymeric material or another polymeric material.

Projections 52 are provided along the surfaces of both of the proximal and distal shells 14, 16. Such projections may be utilized to provide localized regions of increased rigidity or toughness. The projections 52 also provide traction points on the surfaces of the proximal and distal shells 14, 16.

In order to provide ventilation for the user when the knee brace 10 is secured to the leg, so that perspiration may evaporate therethrough, slots or openings 48 are defined between the projections 52 within the proximal and distal shells 14, 16. While both the projections 52 and the slots 48 are shown canted at an angle relative to the horizontal, other suitable configurations will be readily recognized, such as vertically extending slots and projections. The slots or openings 48 also reduce the weight of the knee brace 10 by removing material therefrom and further impart flexibility to portions of the proximal and distal shells 14, 16.

Figure 1:
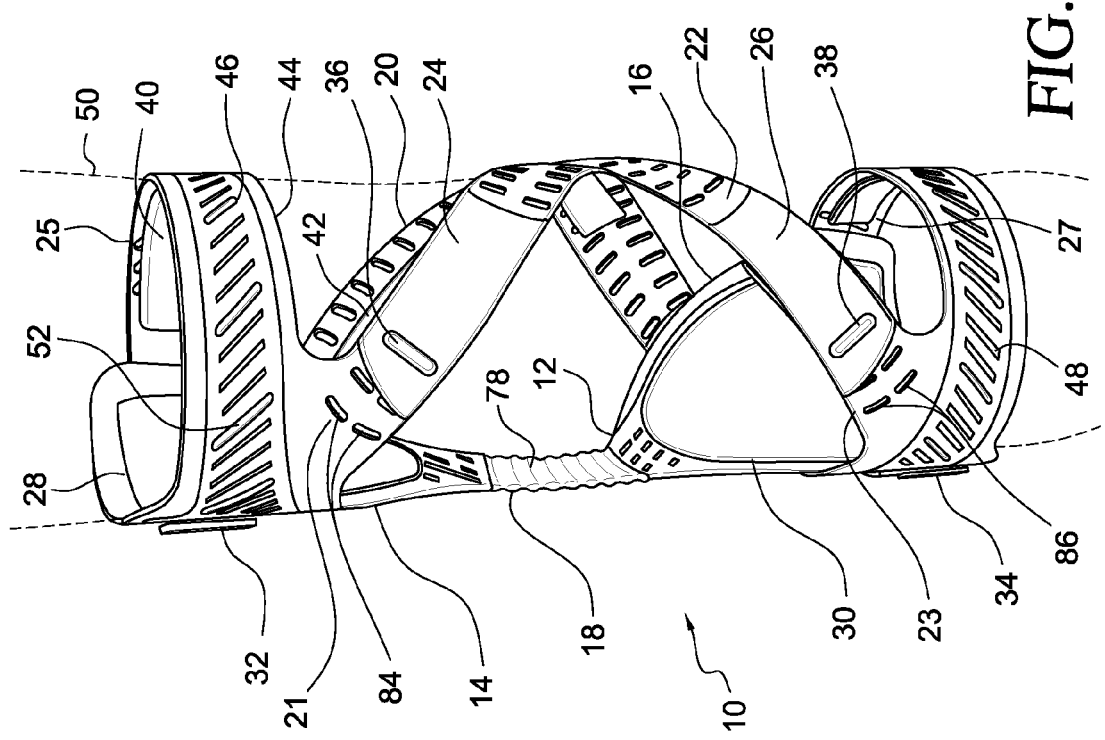
FIG. 1 is a front lateral side perspective view of an embodiment of a wearable device in the form of a knee brace according to the present disclosure.

In a preferred embodiment shown in FIG. 1, the proximal and distal shells 14, 16 are overall substantially flexible to allow the shells to conform to the outline and contours of the leg 50. Specifically, while the proximal and distal shells 14, 16 should have a degree of toughness or rigidity to provide support to the leg and knee joint, as discussed above, they also are flexible enough to allow the proximal and distal shells 14, 16 to conform to the geometry of the leg and knee joint when suitable forces are applied, for example via strapping assemblies.

Figure 3:
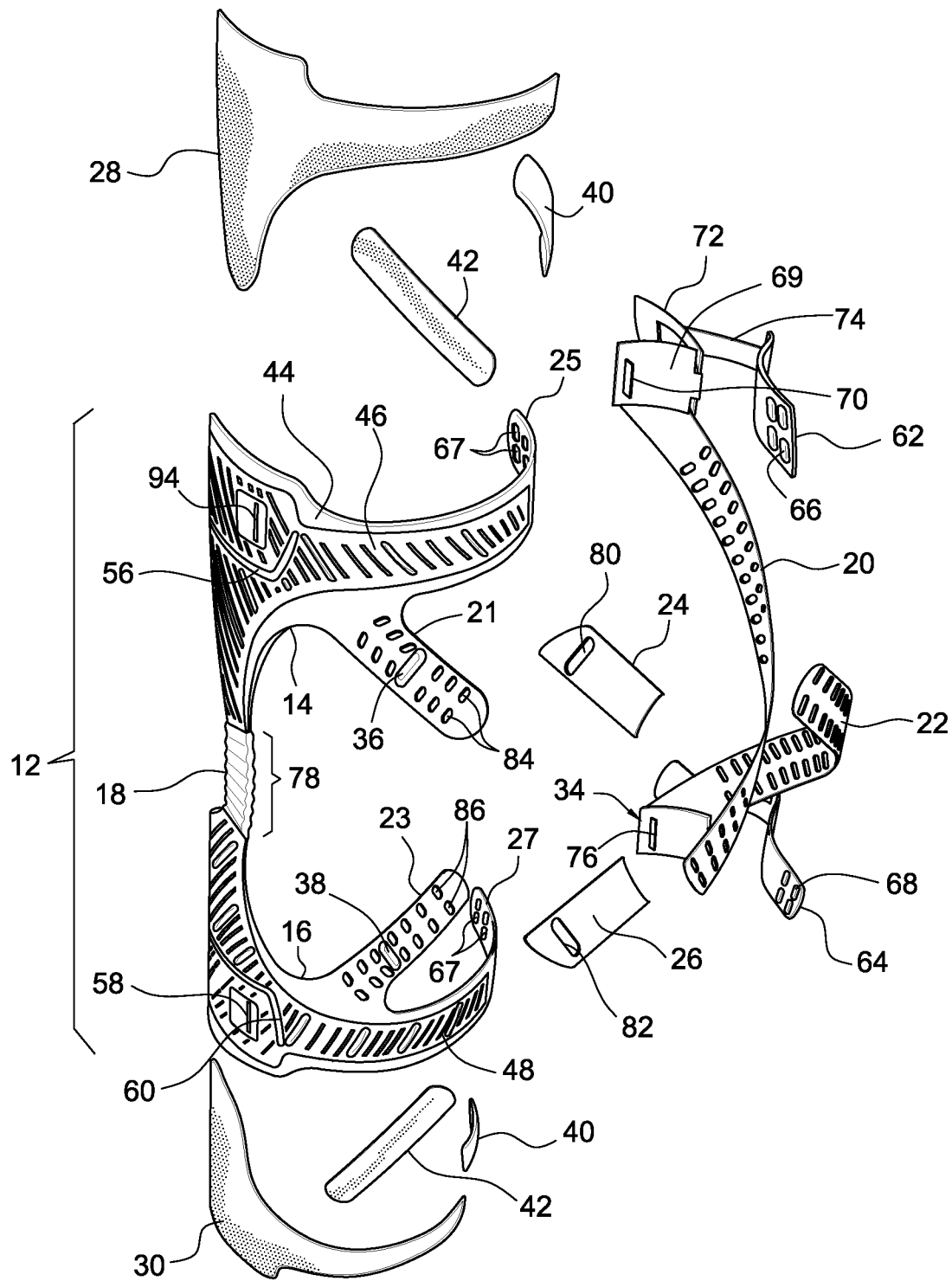
FIG. 3 is a front medial side exploded view of the components of the knee brace of FIG. 1.

Referring to FIGS. 1-3, an additional feature of the embodiment of the knee brace 10 that provides comfort and structures for affixing straps, as will be discussed in detail below, is the secondary, discrete regions of material integrally formed with the proximal and distal shells 14, 16.

As previously discussed, the proximal and distal shells 14, 16 include a discrete rigid, hard, and/or tough region 46 that essentially defines a central portion along the proximal and distal shells 14, 16 and that is rigid and tough enough to provide support to the knee brace 10 and the leg, yet still allows the proximal and distal shells 14, 16 to be substantially flexible so as to conform to the geometry of the leg and knee joint. This region 46 has a first stiffness consistent with these features. In view of the unitary form of the frame, a thickness of the proximal shell may blend into a thickness of the hinge, as well as a thickness of the distal shell may blend into a thickness of the hinge.

In addition, a discrete flexible and/or elastic region 44 generally surrounds, and is integrally formed with, region 46. Discrete region 44 is formed so as to have less stiffness than region 46. In this manner, region 44 essentially provides a compliant, pressure relieving interface between the harder region 46 and the leg and knee joint of the user. The region 44 further may provide additional frictional engagement between the proximal and distal shells 14, 16 and the leg of the user, due to the lower stiffness of the region 44.

The discrete region 44 is distinguished from the region 46 in that it preferably has a softer texture, and that region 46 is also stronger than region 44. More specifically, the discrete region 44 has a hardness that is lower than the hardness of the discrete region 46. The two discrete regions 44, 46 may be integrally formed using any known technique, such as casting, or injection molding.

According to an exemplary embodiment, the region 46 and the region 44 are formed from materials having different hardnesses. In this variation, the region 46 and the region 44 are injection molded thermoplastics that are integrally molded together. An exemplary combination of materials comprises thermoplastic polyurethane elastomers sold under the name ELASTOLLAN by BASF group.

In making the shells 14, 16 of this variation, the main frame 12 is first fabricated by being formed by a first mold. A first material, such as ELASTOLLAN S60D53N, is injected into the mold so as to result in the formation of the main region 46 of the shells 14, 16. The molded main frame 12 is then transferred to another, larger second mold which forms the shape of the shells 12, 14. The main frame 12 is secured and centered in the second mold. A second material, such as ELASTOLLAN C60A10W, is injected into the second mold so as to contact the main frame 12 and form the discrete region 44 therearound. Due to the similarity in composition of the first and second materials, the second material of the region 44 bonds to the first material of the region 46 as it is formed in the second mold. In this variation, the first material has a hardness that is greater than the second material.

A significant advantage to this configuration is that the combination of a flexible, yet tough region 46 with a softer region 44 surrounding and bordering the tough region 46 of the shells 14, 16 provides a substantially comfortable feature to the knee brace.

Another advantage to this variation is that the shells 14, 16 and the region 44, may be pigmented in different colors. This results in an appearance that results in a piping around the periphery of the shells 14, 16 which provides a visually pleasing appearance. For example, the first material used for forming the region 46 of the shells 14, 16 may have a black pigment, whereas the second material used for forming the region 44 may have a gray pigment.

While similar materials are described in connection with this variation, it will be noted that dissimilar materials may also be used. For example, polyethylene, polyurethane and other thermoplastics may be used for forming the main region 46 of the shells 14, 16, and suitable materials such as vinyl, rubber or thermoplastic elastomers may be used for forming the region 44. Other methods for forming the main region 46 of the shells 14, 16 with the region 44 may be found in U.S. Pat. Nos. 5,445,602 and 5,716,335, incorporated herein by reference. Moreover, a soft flexible region may be mechanically adhered, such as by an adhesive, to a shell having ledge, slotted or groove portions upon which the flexible region may be adhered and that does not interlock with any structure of the shell.

Additional comfort may be provided by the utilization of padding 28, 30 between the shells 14, 16 and the leg of the user. Such padding may be ventilated, with for example holes or channels, so that perspiration may evaporate from the skin of the user. Exemplary configurations of ventilated padding are disclosed in U.S. patent application Ser. No. 11/312,330, filed on Dec. 21, 2005, published as U.S. publication no. 2006/0135900 A1 on Jun. 22, 2006, and herein incorporated by reference.

In order to provide additional support to the brace 10 while still allowing the necessary amount of flexion/extension and varus/valgus movement of the knee joint, hinge 18 is continuously formed between the proximal and distal shells 14, 16. Hinge 18 is integrally formed with the shells 14, 16 in any suitable manner, such as by injection molding. Hinge 18 is formed to have a greater stiffness than the shells 14, 16, so as to provide the appropriate amount of resistance and support to the knee joint. This may be accomplished by utilizing a different material for the hinge 18 than the shells 14, 16, and/or by altering the geometry of the hinge.

As shown in FIGS. 1-3, the hinge 18 has a contoured covering 78 that accommodates the geometry of the knee joint. Alternatively, the covering 78 may represent at least one plate covering components formed by the frame which form a hinge. Thus, the hinge may extend out of the anterior/posterior plane and/or the medial-lateral plane, or parallel planes thereto. Alternatively, the hinge may be arranged to limit movement along the medial-lateral plane, and favor only certain degrees of extension and flexion of the knee.

Figure 5:
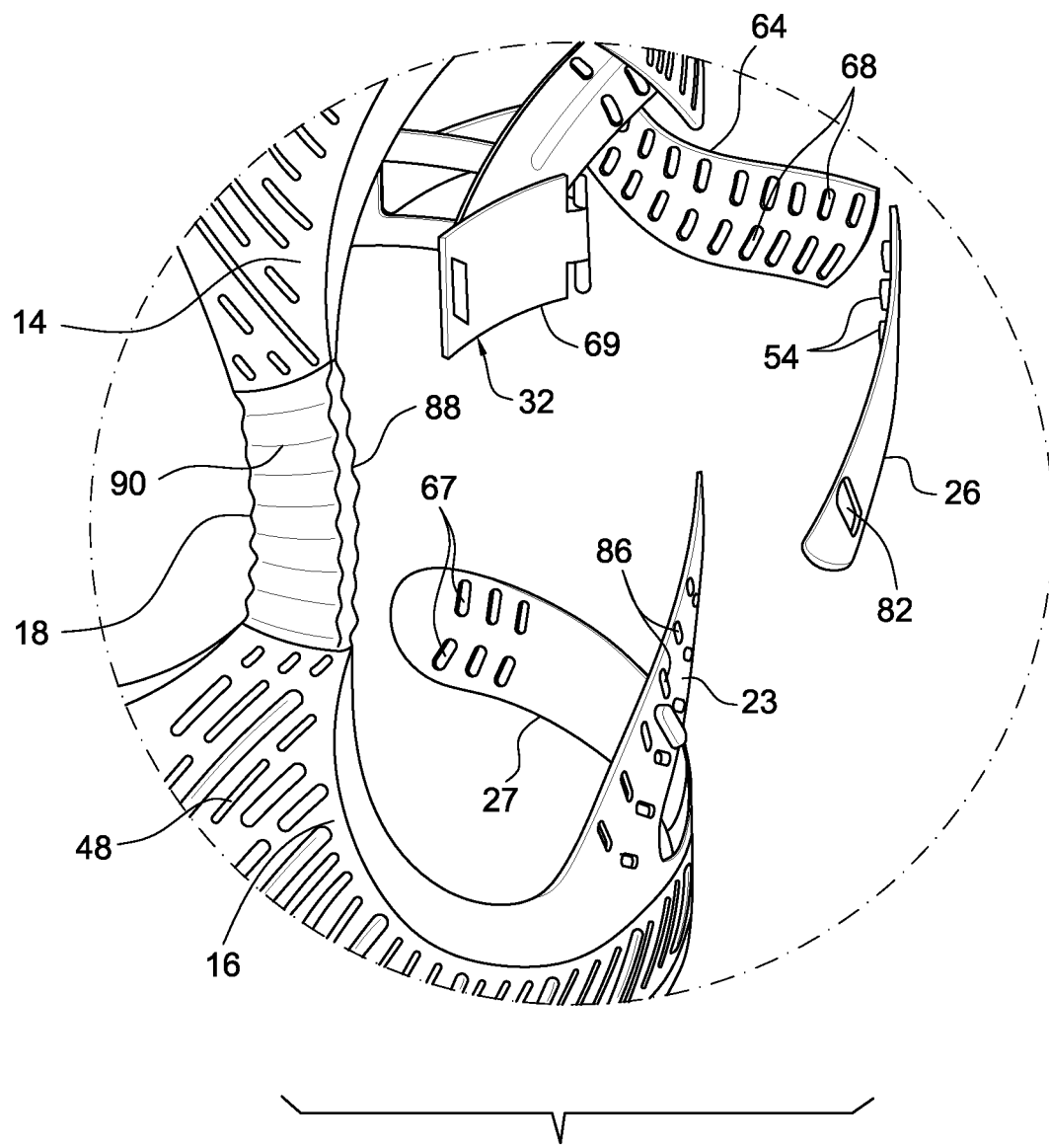
FIG. 5 is a magnified exploded view of the hinge and straps, connectors, and buckles of the knee brace of FIG. 1.

Referring to FIG. 5, the hinge 18 has an undulating profile 88 formed along anterior and posterior faces thereof and an undulating profile formed by side breaks 90 along the lateral and medial facing sides thereof. The undulating profiles aid with flexion of the hinge to provide the desired flexion/extension and varus/valgus movement of the knee joint. For example, the hinge may be slightly biased in the flexion direction in that the hinge geometry has a predetermined bend favoring flexion, and limiting extension. However, the hinge geometry is configured such that the hinge can only bend so far to a certain degree in the flexion direction.

The hinge may also define an undulating profile delimited by breaks formed along lateral and medial facing sides thereof to aid with varus/valgus rotation of the knee brace when the brace is secured to the leg. Or in the alternative, the hinge may be reinforced with elongate ribs running the length of the hinge to resist lateral and medial movement of the leg.

The hinge may be formed and configured to accommodate or facilitate bending of the hinge in certain directions, or limiting the range of motion in certain directions. For example, the hinge may be slightly biased in the flexion direction in that the hinge geometry has a predetermined bend favoring flexion, and limiting extension. However, the hinge geometry is configured such that the hinge can only bend so far to a certain degree in the flexion direction.

Turning now to the arrangements provided to secure the knee brace 10 to a user's leg and knee joint, first and second strap assemblies including first and second straps 20, 22 connect to the proximal and distal shells 14, 16 in a manner providing much versatility for accommodating many different geometries of leg and knee joints. The straps 20, 22 may be formed from any suitable material, such as plastic, so as to be flexible enough to wrap around and configure to the geometry of the leg and knee joint. The straps 20, 22 may be formed in any known suitable manner, such as casting or injection molding. Each of the straps 20, 22 may include a cushion feature 42, such as foam or a textile pad that is secured thereon for enhanced rotational prevention and additional comfort. Of course, cushion feature 42 may be any suitable pad, such as a ventilated pad of the type previously discussed.

With particular reference to FIGS. 1 and 3, the flexible and/or elastic region 44 forms proximal and distal frame segments 21, 23 that protrude from the proximal and distal shells 14, 16 and generally extend towards the distal and proximal shells 16, 14, respectively. Additionally, the flexible and/or elastic region 44 forms a proximal frame strap 25 extending horizontally from the horizontal arcuate proximal frame portion and a distal frame strap 27 extending horizontally from the horizontal arcuate distal frame portion. Each of the proximal and distal frame straps 25, 27 may include a cushion feature 40, such as foam or a textile pad that is secured thereon for enhanced rotational prevention and additional comfort. Of course, cushion feature 40 may be any suitable pad, such as a ventilated pad of the type previously discussed.

The proximal and distal frame segments 21, 23 and frame straps 25, 27 serve as anchor points for the first and second straps 20, 22 in a manner to be described below.

The proximal and distal frame segments 21, 23 define openings 84, 86 therethrough along substantially the entire frame segment. The openings 84, 86 are shown as parallel pairs of slots, however, any suitable configuration, such as parallel single elongated slots, or such as circular or elliptical holes may be utilized. The openings 84, 86 may provide for ventilation, reducing the weight, and/or increasing the flexibility of the frame segments.

The proximal and distal frame segments 21, 23 further include locking projections 36, 38 that extend from the anterior surfaces respectively thereof. The locking projections 36, 38 are illustrated as substantially rectangular projections oriented perpendicularly to a longitudinal direction of the respective frame segments. Of course, any suitable shape or form or arrangement of locking projection may be provided, such as a pair of cylindrical locking projections, or elliptical locking projections.

The proximal and distal frame straps 25, 27 also define openings or slots 67 therethrough. Again, the openings 67 are shown as parallel pairs of slots, however, any suitable configuration, such as parallel single elongated slots, or such as circular or elliptical holes may be utilized.

Like the proximal and distal frame segments 21, 23, and the proximal and distal frame straps 25, 27, the straps 20, 22 define a series of openings 92 provided in a plurality of rows defined along substantially the entire length of the straps. As previously stated the openings 92 are shown as parallel rows or pairs of slots, however, any suitable configuration, such as parallel single elongated slots, or such as circular or elliptical holes may be utilized.

In order to provide a selective positionable connection between the first and second straps 20, 22 and the proximal and distal shells 14, 16, respectively, the first and second strap assemblies may also include first and second strap connectors 24, 26 may be utilized. The first and second strap connectors 24, 26 define a slot or opening 80, 82 located at or near a first end thereof, and further define projections 54 extending from the posterior surface and located at or near a second end opposed to the first end.

Figure 4:
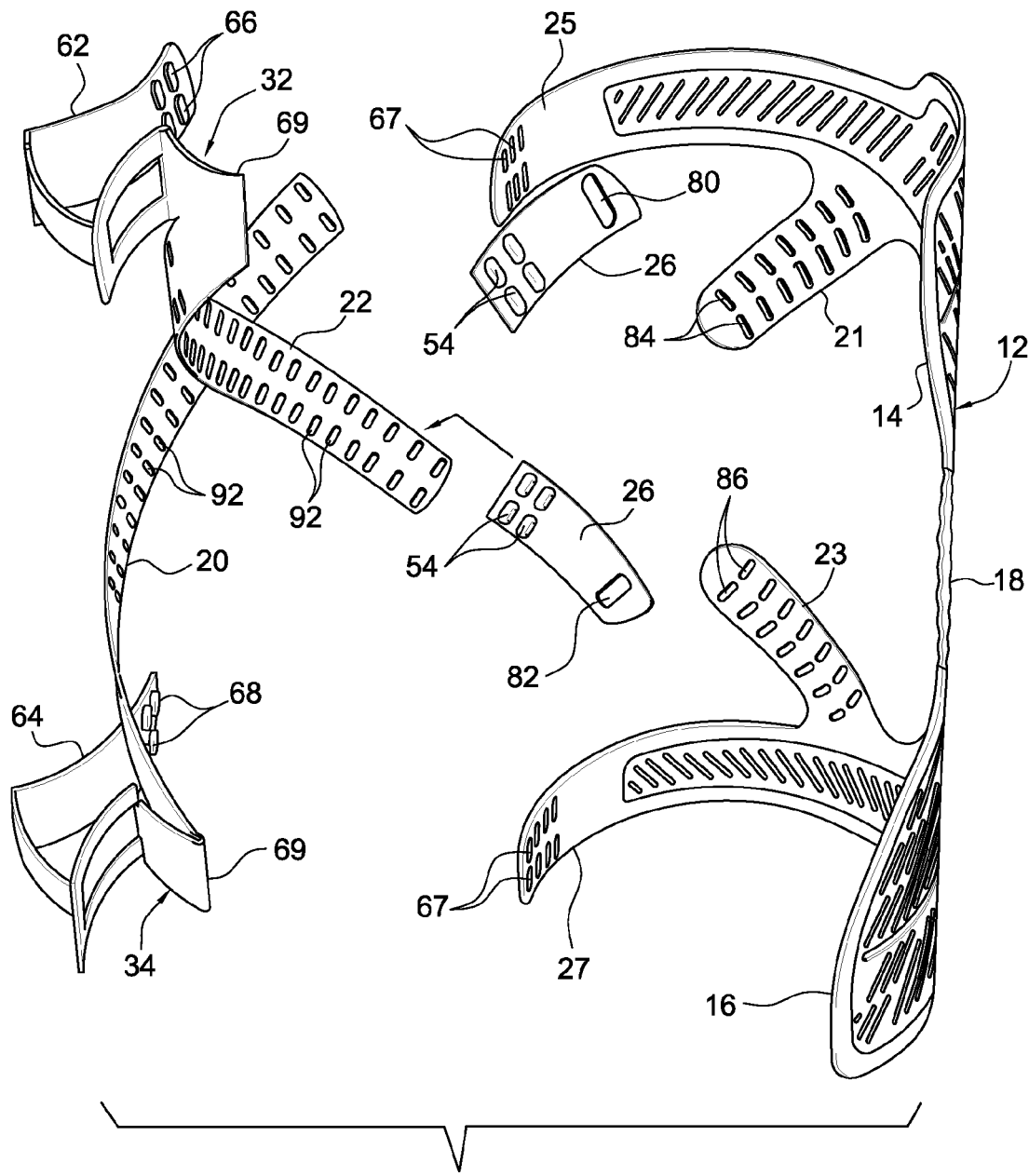
FIG. 4 is a rear medial side exploded view of the frame and straps of the knee brace of FIG. 1.

As shown in FIG. 4, the projections 54 include two sets of pairs of rectangular projections that are shaped and configured to releasably frictionally engage and interlock with any pair of the slots or openings 94 defined in the straps 20, 22. In this manner, the first and second strap connectors 24, 26 may be selectively positioned along the length of the straps 20, 22 in order to effectively adjust the length thereof. Since, as previously mentioned, the openings 94 may have any suitable or desired shape, it will be recognized that the projections 54 may have any corresponding suitable or desired shape as the openings 94 in order to frictionally interlock therewith.

At the opposed ends of the strap connectors 24, 26, the slot or openings 80, 82 are shaped and configured to releasably frictionally fit over the projections 36, 38 of the first and second frame segments 21, 23. Again, it will be recognized that any suitably corresponding shape may be used for the openings 80, 82 and the projections 36, 38. Accordingly, the strap connectors 24, 26 selectively positionably connect the first and second straps 20, 22 to the proximal and distal shells 14, 16.

The strap connectors 24, 26 are formed to be substantially inelastic such that when the first and second straps 20, 22 are connected to the proximal and distal shells 14, 16, little or no stretching, which may lead to a less secure fit of the brace on the leg, occurs.

The strap assemblies may also include proximal and distal buckle assemblies 32, 34 secured to the ends of the first and second straps 20, 22 that are opposed to the ends where the strap connectors 24, 26 are connected. The buckle assemblies 32, 34 define a low profile buckle assembly which locks the straps 20, 22 in position relative to the shells 14, 16 and functions in a manner similar to that described in U.S. Pat. No. 7,198,610. The buckle assemblies 32, 34 each include a first buckle flange 69 integrally formed with, or secured to, the end of the straps opposed to the ends connected via the strap connectors 24, 26.

Each of the first buckle flanges 69 include a projection 70, 76 positioned at or near a first end of the buckle flange 69 along an anterior surface thereof. The projections 70, 76 are rectangularly shaped, but may take any suitable shape or form. The projections 70, 76 and the buckle flanges 69 are configured to releasably frictionally engage a mounting slot 94, 58 and retaining element 56, 60 formed on the respective proximal and distal shells 14, 16. The retaining elements 56, 60 are formed as recesses along the proximal and distal medial side portions of the respective proximal and distal shells 14, 16. The recesses are generally shaped so as to receive the buckle assemblies 32, 34 therein to provide a low profile brace and to reduce the risk of the buckles catching on clothing or other foreign objects.

The mounting slots 94, 58 are shaped to releasably frictionally engage the projections 70, 76 of the buckle flanges 69. As previously mentioned, the shape of the mounting slots 94, 58 may be any suitable corresponding shape to the shape of the projections 70, 76.

Returning to the buckle assemblies 32, 34, which are similarly constructed and illustrated in FIGS. 2-5, a second buckle flange 72 is pivotably connected to a second end opposed to the first end of the first buckle flange 69. The second buckle flange 72 also defines a recess between first and second ends that is shaped and configured to receive a third buckle section 74 therein. The third buckle section 74 is pivotably connected at a first end to the second buckle flange 72 at an end of the second buckle flange 72 opposed to the pivotal connection between the second buckle flange 72 and the first buckle flange.

The third buckle flanges 72 are secured or connected at a second end to respective first ends of proximal and distal flexible extension members 62, 64. The flexible extension members 62, 64 work in concert with the buckle assemblies 32, 34 to selectively lock and secure the brace 10 to the user's leg and knee joint, as will be described in more detail below.

The flexible extension members 62, 64 respectively include pairs of projection members 66, 68 at or near second ends thereof opposed to the first ends. The projection members 66, 68 are formed along posterior surfaces thereof and are configured in the same manner as projections 54 described above. Similarly to projections 54, the projection members 66, 68 are configured to frictionally, releasably engage and interlock with selective pairs of the openings 67 defined in the proximal and distal frame straps 25, 27. It will again be recognized that any suitable corresponding shapes or configurations for the openings 67 and projection member 66, 68 may be utilized. In this manner, the effective length of the respective buckle assemblies and flexible extension member may be increased or decreased as needed.

It will be noted that the components of the buckle assemblies 32, 34 and the flexible extension members 62, 64, as well as the straps 20, 22 may all be integrally injection molded together as a unitary piece or unit. Alternatively, the components may be injection molded separately and connected utilizing traditional pivot pins for the pivoting connections.

In use, a user can place the knee brace 10 on the leg with the proximal shell 14 engaging the thigh and the distal shell 16 engaging the shin and calf. The straps 20, 22 may be connected to the proximal and distal shells 14, 16 via the first and second strap connectors 24, 26, and the first and second flexible extension members 62, 64. The connections of the straps 20, 22 to the proximal and distal shells 14, 16 at the first and second frame segments 21, 23 and the proximal and distal frame straps 25, 27 may be adjusted in order to provide the necessary amount of forces to provide unloading of the lateral component of the knee joint.

Once the straps 20, 22 have been connected to the proximal and distal shells 14, 16, the proximal and distal buckle assemblies 32, 34, and in particular, the first buckle flanges 69 and projections 70, 76, may be engaged with the mounting slots 94, 58 and retaining elements 56, 60 formed on the respective proximal and distal shells 14, 16. The flexible extension members 62, 64 bend to allow the straps 20, 22 and the buckle assemblies 32, 34 to encircle the posterior portions of the leg.

Once this is accomplished, the straps 20, 22 basically form a circumferential shape, along with the proximal and distal shells 14, 16, to surround the anterior and posterior portions of the thigh/hamstring and shin/calf. In order to secure the knee brace 10 in position, the buckle assemblies 32, 34 are moved from a disengaged position to an engaged position.

As shown in FIG. 2, the buckle assemblies 32, 34 are in a disengaged position. The second buckle flange 72 acts as a lever arm that may be manipulated in and out of essentially flush engagement with the first buckle flange 69 to either engage or disengage the buckle assemblies 32, 34 in a manner that will be recognized by a skilled artisan.

As illustrated, the buckle assemblies 32, 34 include a curved profile such that they conform to the leg of a wearer of the brace. This imparts a more streamlined buckle assembly and further prevents the buckle assembly from snagging on clothing or acting as an impediment to the wearer of the brace.

It will be recognized that resilient releasable locking structures may be provide to the buckle assemblies 32, 34 in order to prevent the accidental disengagement of the buckle assemblies. Such releasable locking structures are described in detail in U.S. Pat. No. 7,198,610.

In a variation of the straps, as illustrated in FIG. 6, an elongate strap 100 is formed with at least two discrete regions which are continuously formed without interruption. The first region 102 is formed with a first polymeric material, and generally defines the longitudinal core of the strap 100. A second region 104 forms a peripheral edge portion to the first region, and is formed from a polymeric material which is less rigid than a polymeric material used to form the first region 102. While the second region is preferably injection molded over the periphery of the first region and interlocked with or bonded to the first region, other suitable means may be employed to secure the second region to the first region of the strap.

The first region may be configured so that it is substantially inelastic, or alternatively elastic, depending on the usage of the wearable device. The peripheral edge portion is preferably formed as a soft, pressure relieving feature for the wearer of the device.

The strap 100 may form a plurality of openings 106 which have an integrally formed grommet or reinforcement ring 108 which is formed from a material (e.g., polymeric material) that may be either tougher or alternatively less rigid than the first polymeric material of the strap 100. The properties of the ring 108 can be adapted to the particular usage, such that a ring tougher than the first region may be formed if the first region itself may tear upon repeated usage of engaging the openings with a corresponding hook or other attachment element, or in the alternative a soft or flexible ring can be used to assure better locking with a hook or other attachment element by maintaining the attachment element in the opening.

A plurality of protrusions 110 may be integrally formed on the first region 102 that are arranged to engage the openings 106 or openings formed on the frame of the brace. These protrusions 110 may be formed from the first polymeric material, or alternatively from another polymeric material continuously and integrally formed with the first region 102. Other means may be provided to form, attach or adhere the protrusions to the strap 100, such as fasteners, adhesives or other suitable means.

In accordance with another embodiment of the device, the device is formed from first and second frame assemblies which together form a hinge. In observing the device 10 depicted in FIGS. 1-5, the hinge 18 may be formed by a combination of first and second connecting portions belonging to the first and second frame assemblies 14, 16, respectively, and a covering 78 installed or in combination with the hinge 18.

Turning to FIG. 7, one embodiment of a hinge is shown by way of hinge 200, which could be adapted in the embodiment of FIGS. 1-5. The hinge 200 involves a first connecting portion 202 having a first end integrally provided without interruption from the proximal frame portion (not shown). The first connecting portion 202 includes an elongate central portion 206 and a perimeter edge portion 208 extending along at least part of the periphery of the central portion 206. The hinge 200 also includes a second connecting portion 204 integrally provided without interruption from the distal frame portion (not shown), and likewise includes an elongate central portion 210 and a flexible perimeter edge portion 212 extending along at least part of the periphery of the central portion 210.

The peripheral edge portions are formed using a less rigid polymeric material than the material forming the central portions in both the first and second connecting portions, thereby forming a pressure relieving section to the hinge. It will be noted that the central portions can be formed from a polymeric material, fiber reinforced material, or any other suitable material a non-interrupted and continuous structure with the peripheral edge portion and the corresponding proximal and distal frame portions.

Second end portions 214, 216 of the first and second connecting portions 202, 204 each define a head having a generally circular gear portion 218, 220. The second end portions 214, 216 are pivotably mounted about pivot points 230, 232 of a covering 228 such that the gear portions 218, 220 mesh with one another.

Each second end portion 214, 216 is provided with first stop structures 224, 234. The first stop structures 224, 234 are located on an anterior or front facing side of the hinge 200 and are arranged to limit rotation of the hinge 260 in the anterior or forward direction of the hinge in combination with stop face 226 formed on the covering 228. The second stop structure 236 is formed on a generally posterior or rear facing side of the hinge, and is arranged to limit rotation in the posterior or backward direction of the hinge.

Apertures 230, 232 may be formed in the covering 228 along the path of the stop structures as the gear portions 218, 220 rotate. These apertures are adapted to receive a screw or pin. The screw or pin can be provided to block or engage one of the first and second stop structures to further limit rotation of the hinge.

Strengthening ribs 237 may be provided along the first and second central portions 206, 210 so as to reinforce the first and second connecting portions 202, 204 from lateral and medial movement of the hinge 200. Alternatively, the ribs 237 may be replace with openings having a similar profile so as to reduce weight and enhance flexibility of the first and second connecting portions.

FIG. 8 illustrates another embodiment of a hinge 240. In this embodiment, a first connecting portion 241 includes an elongate central portion 242 with a peripheral edge portion 244, and an end portion having a generally circular head portion 245. A second connecting portion 243 includes an elongate central portion 246 with a peripheral edge portion 248, and an end portion having a generally circular head portion 247. The central portions 242, 246, and peripheral edge portions 244, 248 of the first and second connecting portions 241, 243 may be similarly formed as in the embodiment of FIG. 7. The first and second connecting portions 241, 243 are pivotally connected at their head portions 245, 247, so that the first and second connecting portions 241, 243 are individually connected to one another. A covering plate 252 may be used to cover the circular head portions 245, 247.

In view of the above description, an exemplary embodiment of a wearable device providing motion control is described. Such a device may be formed substantially in a single unitary frame assembly or in multiple unitary frame assemblies by virtue of injection molding and overmolding techniques. Additionally, frame assemblies described herein may be combined in combination with other frame assemblies or components which are not provided in unitary form. Other components of the device, including the straps and buckle assemblies, may also be injection molded, either integrally with or separately from the frame assemblies.

As a result of the solutions provided and described herein, and all equivalents thereof, the device may be provided off-the-shelf or over-the-counter to a large body of the populace at a relatively low cost, and regardless of the varied geometries of the legs and knees of the many different users.

C. Conclusion

While a particular embodiment of a wearable device is discussed above utilizing all or substantially all injection molded parts, the components of the knee brace described herein may be formed in any suitable manner recognized by a skilled artisan, such as casting, machining, stereolithography, or any other suitable process.

The disclosed embodiment of an wearable device provides an improved knee brace that is lightweight and low cost and has a lower profile than a typical brace.

It is understood that the size of the device and the components thereof can be adjusted so that an even larger number of different users having different sized joints and body parts may benefit from the present design.

It is also understood that the locations of the various interlocking projections and openings can be alternated from those shown, such that the positions of the openings and locking projections may be swapped from the positions as illustrated herein.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a knee brace in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A method for forming a strap having first and second regions continuously joined to each other without interruption, comprising the steps of:
   forming the first region by injecting a first polymeric material into a first mold, the first region defining a longitudinal core of the strap;
   forming the second region by injecting a second polymeric material in a second mold about peripheral edge portion to the first region;
   wherein the first polymeric material is a first thermoplastic elastomer, and the second polymeric material is a second thermoplastic elastomer;

wherein the first and second polymeric materials are integrally molded together and chemically bonded at least at an interface between the first and second regions due to a similarity in composition of the first and second polymeric materials, the first thermoplastic elastomer having greater rigidity than the second thermoplastic elastomer.

2. The method according to claim 1, including the step of bonding the second polymeric material to the first polymeric material as the second polymeric material is formed into the second region.

\* \* \* \* \*